United States Patent [19]
Devos et al.

[11] Patent Number: 6,099,511
[45] Date of Patent: Aug. 8, 2000

[54] MANIFOLD WITH CHECK VALVE POSITIONED WITHIN MANIFOLD BODY

[75] Inventors: Gilles J. Devos, Voisins le Bretonneux, France; William Padilla; Fred P. Lampropoulos, both of Sandy, Utah

[73] Assignee: Merit Medical Systems, Inc., South Jordan, Utah

[21] Appl. No.: 09/273,033

[22] Filed: Mar. 19, 1999

[51] Int. Cl.⁷ ................................................ A61M 5/00
[52] U.S. Cl. ........................ 604/246; 604/248; 604/30; 604/82
[58] Field of Search .................................. 604/246, 247, 604/248, 30, 32, 82, 83, 236, 183, 184

[56] References Cited

U.S. PATENT DOCUMENTS

| | | | |
|---|---|---|---|
| 5,158,539 | 10/1992 | Kolff et al. | 604/31 |
| 5,356,375 | 10/1994 | Higley | 604/30 |
| 5,423,751 | 6/1995 | Harrison et al. | 604/83 |
| 5,533,978 | 7/1996 | Teirstein | 604/183 |
| 5,573,515 | 11/1996 | Wilson et al. | 604/236 |
| 5,618,268 | 4/1997 | Raines et al. | 604/82 |

*Primary Examiner*—John D. Yasko
*Attorney, Agent, or Firm*—Workman, Nydegger & Seeley

[57] ABSTRACT

A manifold has a manifold body defining a fluid flow pathway therethrough. The manifold body has a plurality of valves, at least one of which is a check valve. The manifold is coupled at one end to a syringe or other fluid delivery means and to an opposing end to a catheter or other fluid receiving means. By being positioned within the manifold body, the check valve is reinforced and stabilized within the manifold.

35 Claims, 8 Drawing Sheets

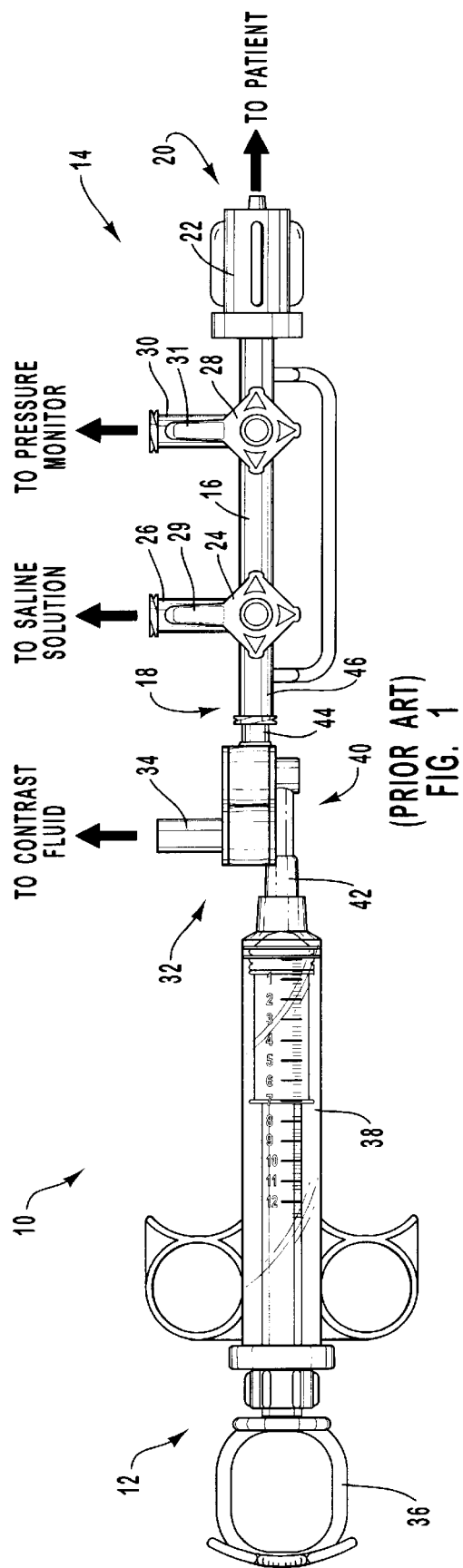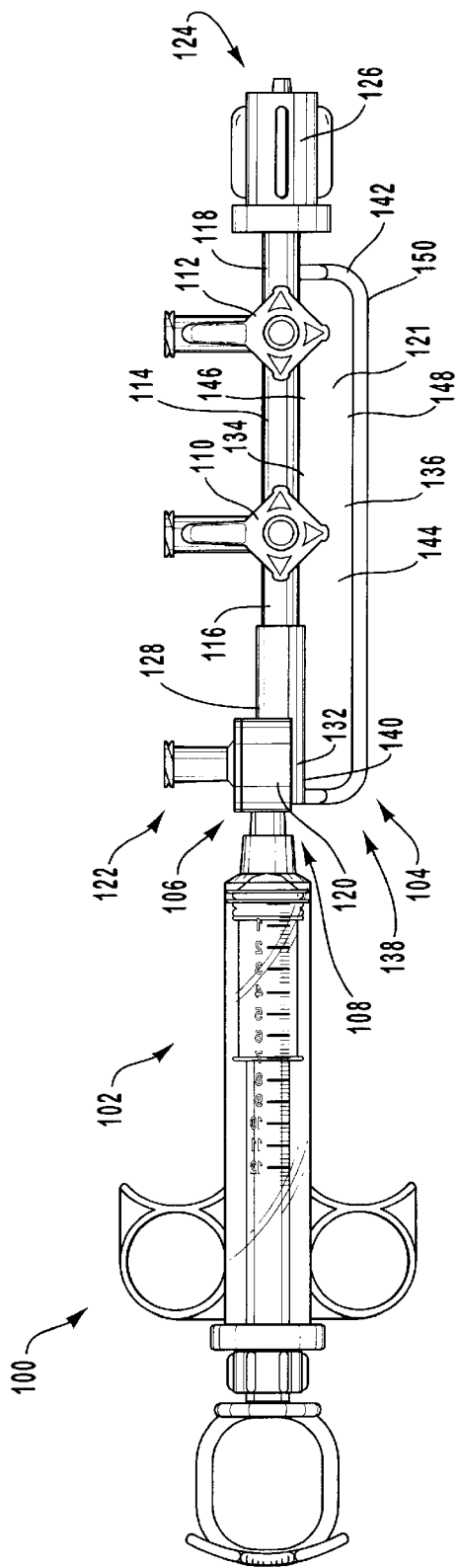

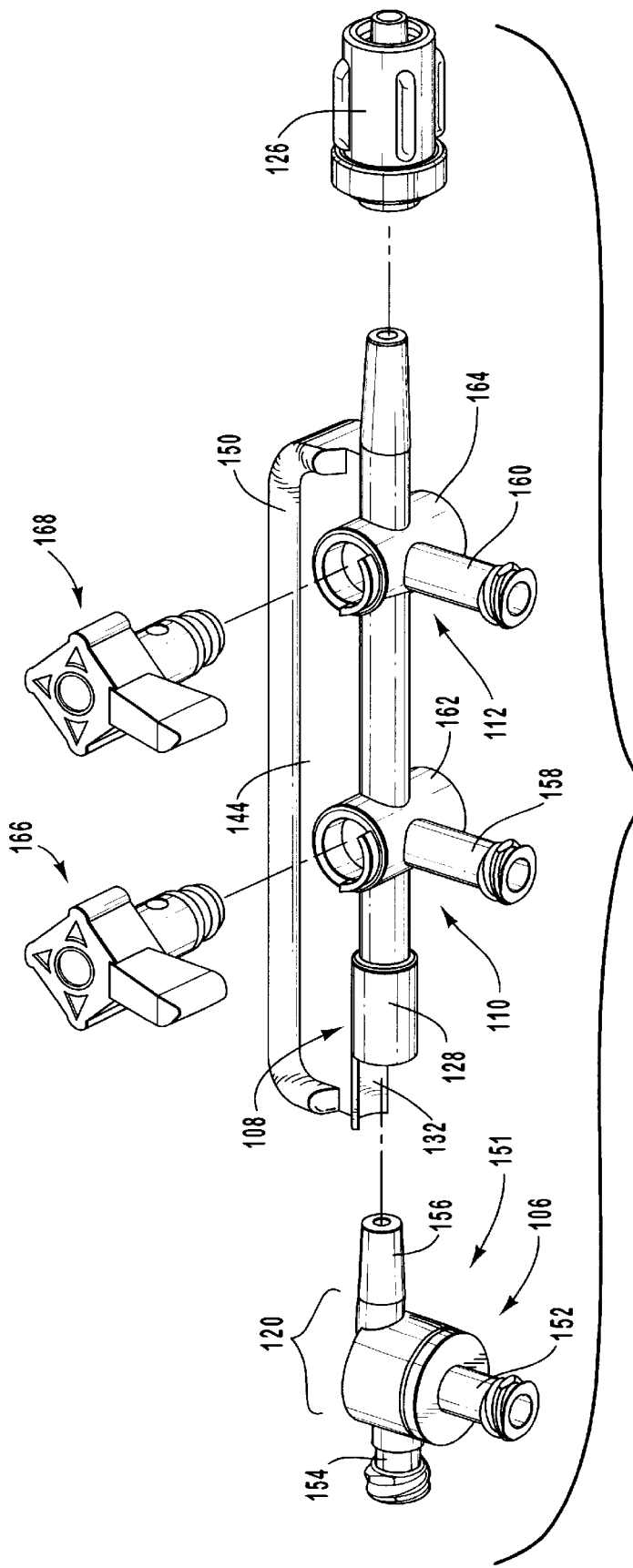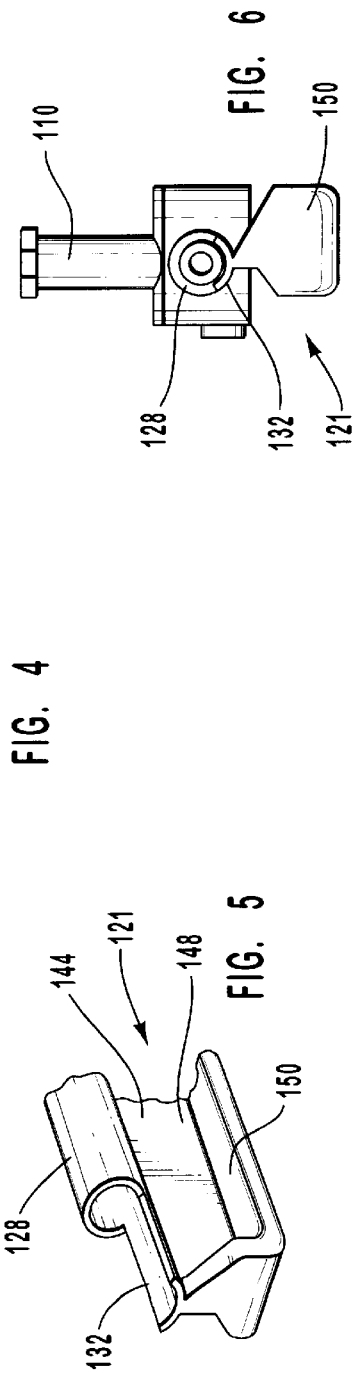

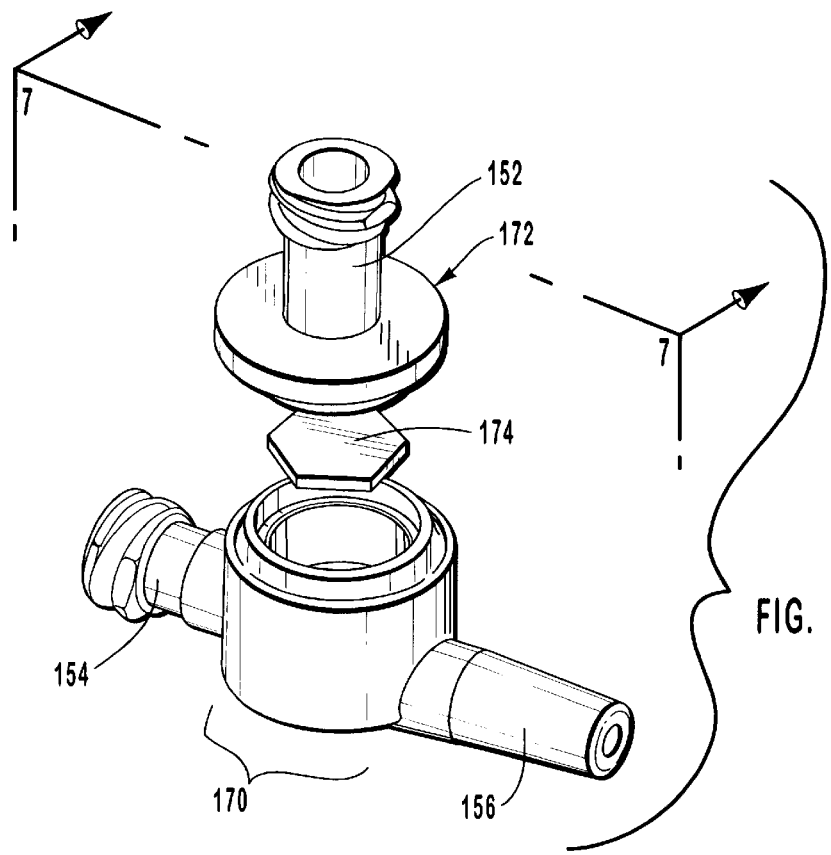
FIG. 7
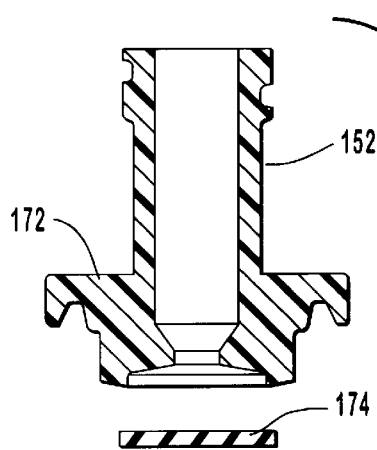
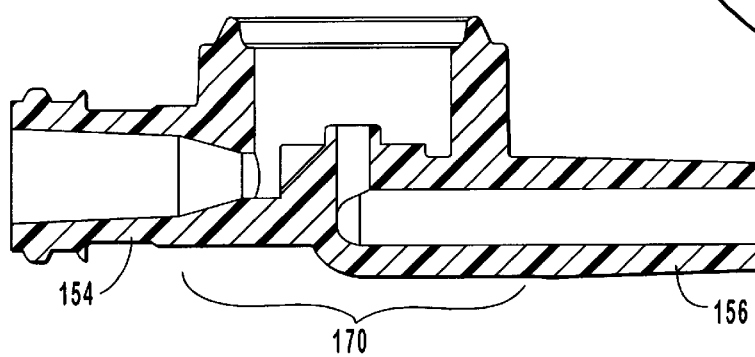
FIG. 8

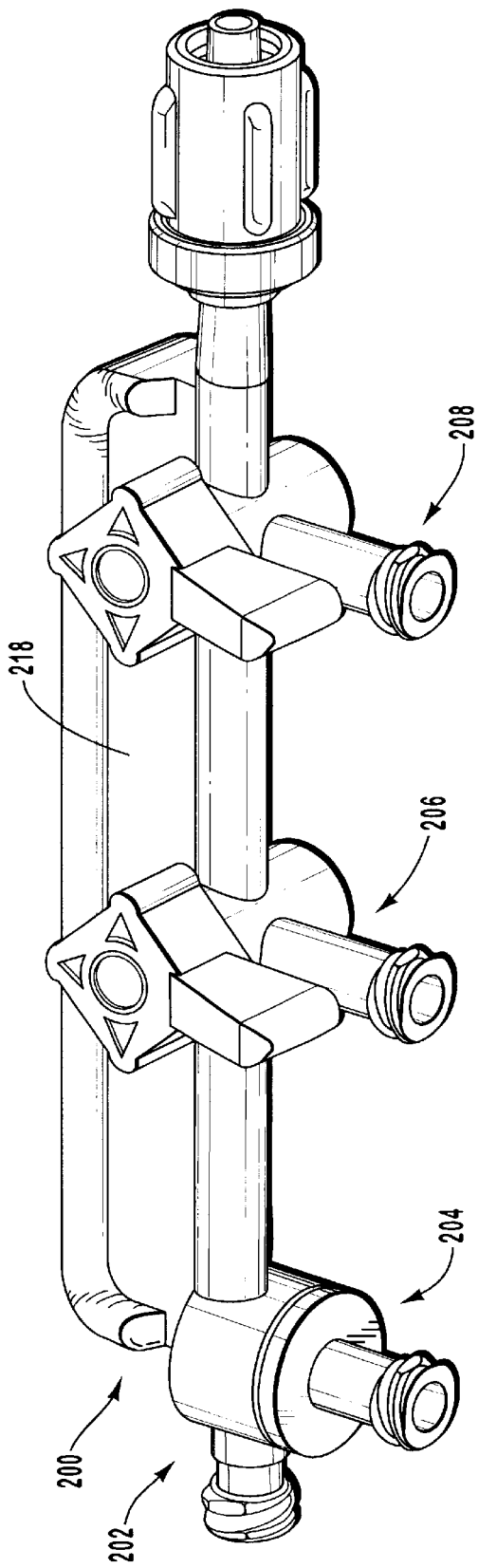
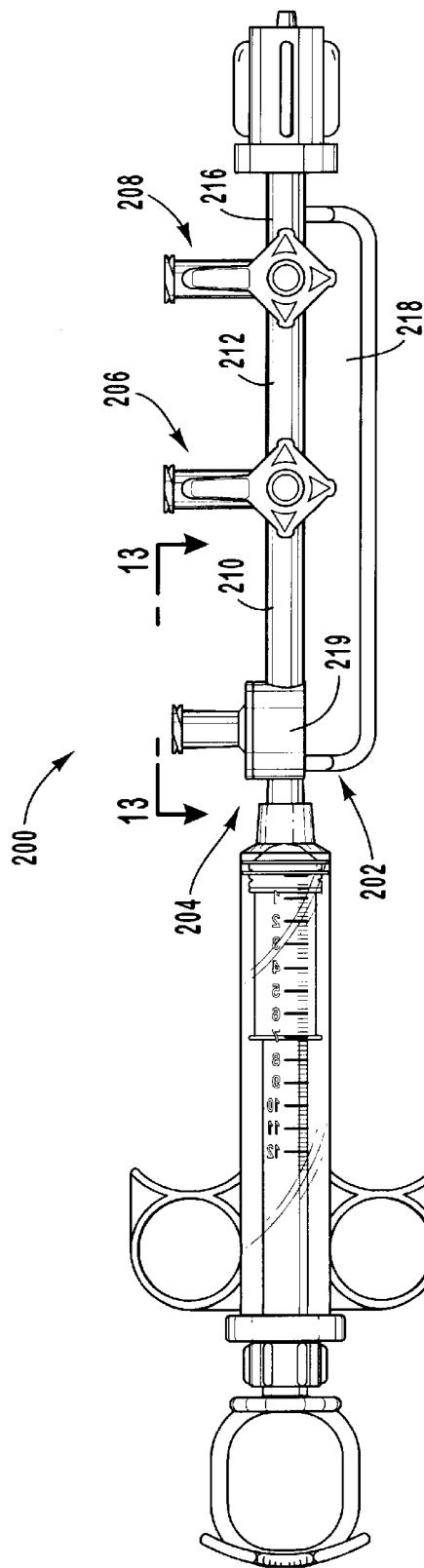

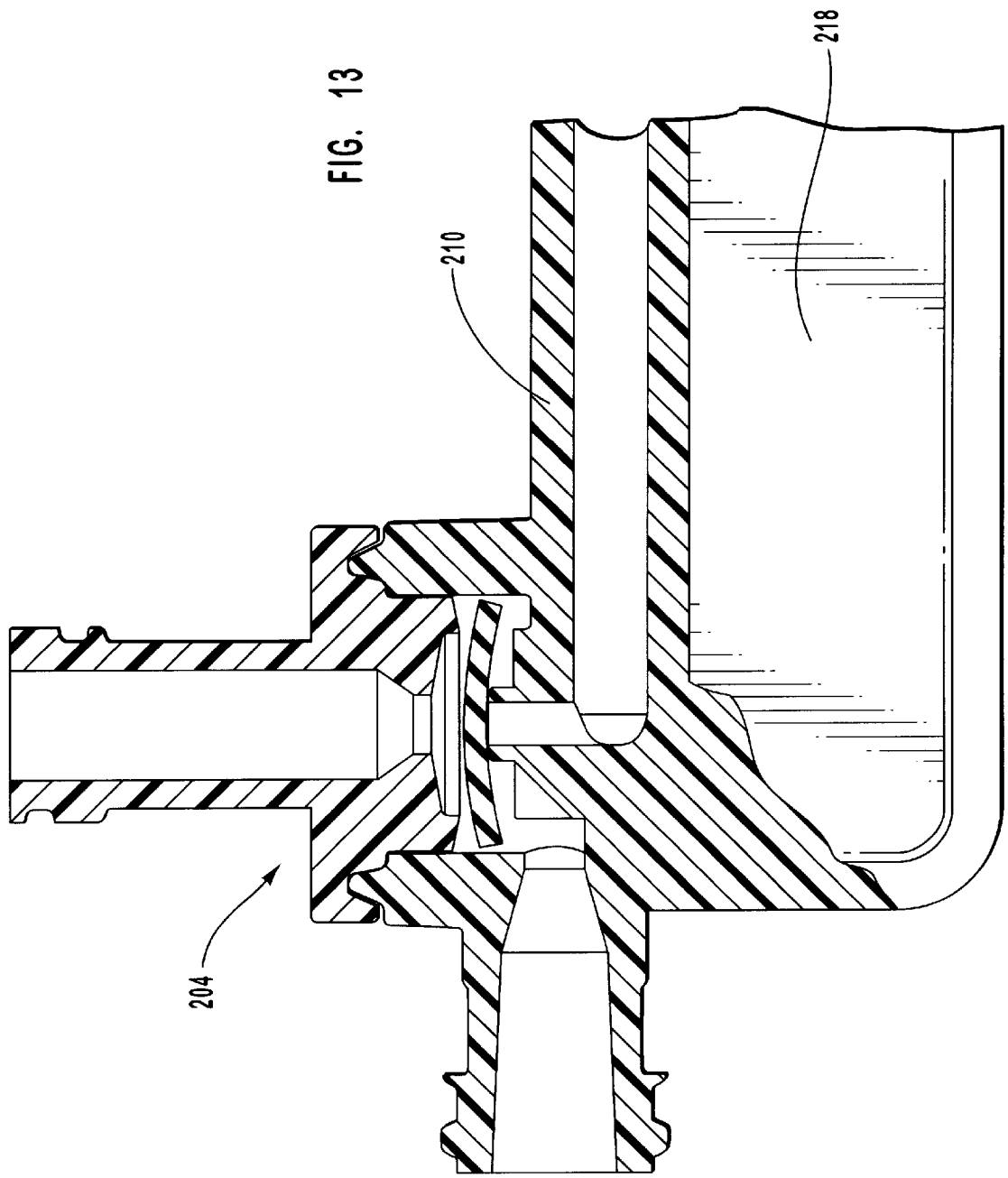

MANIFOLD WITH CHECK VALVE POSITIONED WITHIN MANIFOLD BODY

BACKGROUND OF THE INVENTION

1. The Field of the Invention

This invention relates to valves. More specifically, this invention relates to valves employed in manifolds used during administration of medical liquids to a patient.

2. The Relevant Technology

During angiography and angioplasty procedures (hereinafter, "angio procedures"), a fluids administration set may be employed. During such an angio procedure, a femoral artery site or other site is prepared by a physician. Site preparation is typically performed by injecting a local anesthetic at the femoral artery penetration site to numb the area. An introducer is then used to puncture the epidermis and arterial wall thereunder so as to access the femoral artery. A guide wire is introduced into the artery, and the introducer is removed.

After the removal of the introducer, a sheath is typically inserted into the area where the introducer was removed. The sheath protects the femoral artery site during the angio procedure. A guiding catheter is then slid through the sheath and femoral artery and the catheter is advanced to the heart of the patient. After the catheterization of the patient, a fluids administration set is attached to the guiding catheter for administration of fluids during the angio procedure.

Fluids administration set 10 of FIG. 1 is a depiction of a fluids administration set which is typical in angio procedures. As to the typical aspect of such procedures, FIG. 1 will now be explained. Fluids administration set 10 features a syringe 12 connected to a catheter manifold 14. Catheter manifold 14 has a manifold fluid tube 16 for moving a variety of pressure laden fluids through catheter manifold 14.

Manifold 14 has a proximal end 18 and a distal end 20. At distal end 20 of manifold 14, opposite syringe 12, is a rotating adaptor 22 which connects a catheter (not shown) to manifold 14 and through which various fluids pass intracorporeally to a patient undergoing an angio procedure.

Saline solution occlusion stopcock 24 selectively directs fluid between manifold tube 16 and saline solution port 26. Saline solution port 26 is in fluid communication with a saline solution container (not shown) such as a saline solution bag. Port 26 allows access to saline for flushing the aforementioned catheter with saline so as to clear the catheter of any particulate or thrombosis. Pressure monitor occlusion stopcock 28 selectively directs fluid between manifold fluid tube 16 and pressure monitor port 30.

Stopcocks 24, 28, each have a handle thereon which is rotated to direct the flow of pressure laden fluids through catheter manifold 14. In order to operate a stopcock to stop a fluid from passing through the stopcock, the associated handle is turned toward a fluid line so as to point at the fluid line. When so pointed, the stopcock valve closes and prevents fluid in the pointed at line from passing through the stopcock. In FIG. 1, each of the stopcock handles are pointed toward respective ports. This permits fluid traveling through manifold fluid tube 16 to pass through each of the two stopcocks, but not through ports 26 and 30.

Pressure monitor port 30 is in fluid communication with a pressure monitor (not shown) which includes a transducer which measures different pressures in the catheterized heart. In order for this pressure measurement to take place, the handle 31 of pressure monitor occlusion stopcock 28 must be turned to point toward syringe 12 so as to permit fluid to pass from the catheter through port 30 and on to the transducer for sensing and measurement of the heart pressures.

At a proximal end 18 of manifold 14, a check valve 32 is coupled between syringe 12 and manifold 14. A tube (not shown) communicates contrast media from a contrast media fluid source (not shown), to port 34 of check valve 32. Upon retraction of plunger 36 of syringe 12, the contrast fluid selectively flows through valve 32, into syringe 12. Upon compression of syringe 12, the contrast fluid then flows through valve 32, manifold 14 and a catheter coupled to manifold 14 and then into the circulatory system of the patient. When contrast media is injected into the coronary arteries for fluoroscopy, the contrast is visible within the patient and aids in diagnostics.

In order to inject contrast media into the patient, the handles of stopcocks 24, 28 should be pointed toward respective ports 26, 30 as illustrated in FIG. 1 so that contrast media ejected from syringe 12 will pass through both valve 32 and manifold 14. Upon compression of plunger 36 into fluid filled barrel 38, fluid is dispelled into the patient through manifold tube 16 and via the intracorporeally inserted catheter (not shown).

Check valve 32 has a main valve chamber 40, a fluid inlet port 42 coupled to main valve chamber 40, and a fluid outlet port 44 coupled to main valve chamber 40. Fluid inlet port 42 is coupled to syringe 12 through the use of interlocking male and female Luer lock members. Outlet port 44 is tapered so as to be pressed into inlet port 46 of fluid tube 16 and secured thereto through the use of an adhesive.

One advantage of check valve 32 is that the practitioner is not required to turn a stopcock in order to selectively allow fluid to flow therethrough. Instead, the practitioner is merely required to retract plunger 36 of syringe 12, thereby creating a negative pressure within barrel 38, which causes fluid to flow through port 34 from a source of contrast fluid, and into syringe 12. Then, also without turning a stopcock, the practitioner can compress plunger 36 into syringe 12, thereby releasing fluid into the circulatory system of the patient. Thus, contrast fluid can be injected into the patient's circulatory system by retracting plunger, then compressing plunger, rather than requiring the opening of a stopcock to allow fluid into syringe 12 and turning a stopcock to deliver fluid to manifold 14.

However, one difficulty with check valve 32, is that outlet port 44 of valve 32 is particularly susceptible to breakage and other damage during the use of system 10. As the practitioner manipulates syringe 12 in order to fill syringe 12 with fluid and dispel fluid therefrom, the practitioner must grip system 10 tightly and often push with significant force against plunger 36 of syringe 12 in order to force dispel within syringe 12 into the circulatory system of the patient.

As the practitioner compresses fluid within syringe 12 by inserting plunger 36 with such force into barrel 38, the practitioner often holds manifold 14 in one hand. The practitioner thus presses against plunger 36 with one hand while holding manifold 14 in another hand. Consequently outlet port 44 of valve 32 presses with significant force against inlet port 46 of manifold 14, stressing the connection between outlet port 44 and inlet port 46 and particularly stressing outlet port 44.

In addition, as the practitioner presses against plunger 36 with one hand while holding manifold 14 with another hand, it is not uncommon for the practitioner to bend syringe 12 at least slightly with respect to manifold 14. This bending action places particular stress on outlet port 44 of valve 32, which is positioned between syringe 12 and manifold 14.

The bending and compressive forces on outlet port 44 of valve 32 can break, crack or otherwise damage outlet port 44. Such damage can result in the loss of fluid from system 10 during an angioprocedure and may require replacement of valve 32 or both valve 32 and manifold 14 during such an angioprocedure. Such loss of fluid and replacement is inconvenient and time consuming and may require decoupling and recoupling of a variety of different fluid sources and systems before the procedure can be resumed.

SUMMARY AND OBJECTS OF THE INVENTION

It is an object of the invention to provide an improved manifold.

It is another object of the invention to provide a manifold having a body with a check valve therein.

It is another object of the invention to provide a catheter manifold in which a check valve is supported within a body of the catheter manifold.

It is another object of the invention to provide a manifold having a manifold body with a check valve integrally coupled to at least one other valve of the manifold.

A manifold of the present invention features a manifold body having a proximal end and a distal end. The manifold body defines a fluid flow pathway extending between the proximal and distal ends thereof. The manifold body includes a plurality of valves, including a check valve and one or more additional valves. The additional valves may be stopcock-actuated valves, for example. The manifold is selectively coupled to a catheter or other fluid receiving means and to a syringe or other fluid delivery means.

The positioning of the check valve within the body of the manifold significantly reduces the potential for damage to the check valve during use. The connection between the check valves and the other structures on the manifold body is reinforced against damage caused during compression of the syringe plunger and during bending of the syringe with respect to the manifold.

The check valve comprises a main valve chamber and a plurality of ports coupled to the main valve chamber. In order to further prevent damage to the check valve, the invention further comprises support means coupled to the main valve chamber of the check valve for supporting the main valve chamber. A variety of different examples of such support means are available.

In one embodiment, the support means comprises the manifold body including a seat coupled to the main chamber of the valve. The seat is configured to receive the main chamber of the valve in a mating relationship. In another embodiment, the support means comprises a rigid support plate coupled to the manifold body.

By positioning the check valve within the manifold body, the connection between the check valve and additional valves within the manifold is strengthened significantly. In addition, the seat and/or rigid plate coupled to the main chamber of the check valve provides significant stability and reinforcement.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 1 is a side view of a prior art fluid administration set.

FIG. 2 is a side view of a fluid administration set of the present invention.

FIG. 4 is an exploded view of the manifold of the fluid administration set shown in FIG. 2.

FIG. 5 is a cut away perspective view of the seat of the manifold body shown in FIG. 4.

FIG. 6 is an end view of the seat of the manifold body shown in FIG. 5.

FIG. 7 is an exploded view of the embodiment of the valve shown in FIG. 4.

FIG. 8 is a cross-sectional view of the valve shown in FIG. 7.

FIG. 11 is a perspective view of another manifold of the present invention, the manifold having an integral check valve.

FIG. 12 is a side view of a fluid administration set employing the manifold of FIG. 11.

FIG. 13 is a cross-sectional cutaway view of the proximal end of the manifold shown in FIGS. 11 and 12.

DETAILED DESCRIPTION OF THE PREFERRED EMBODIMENTS

Figure 3:
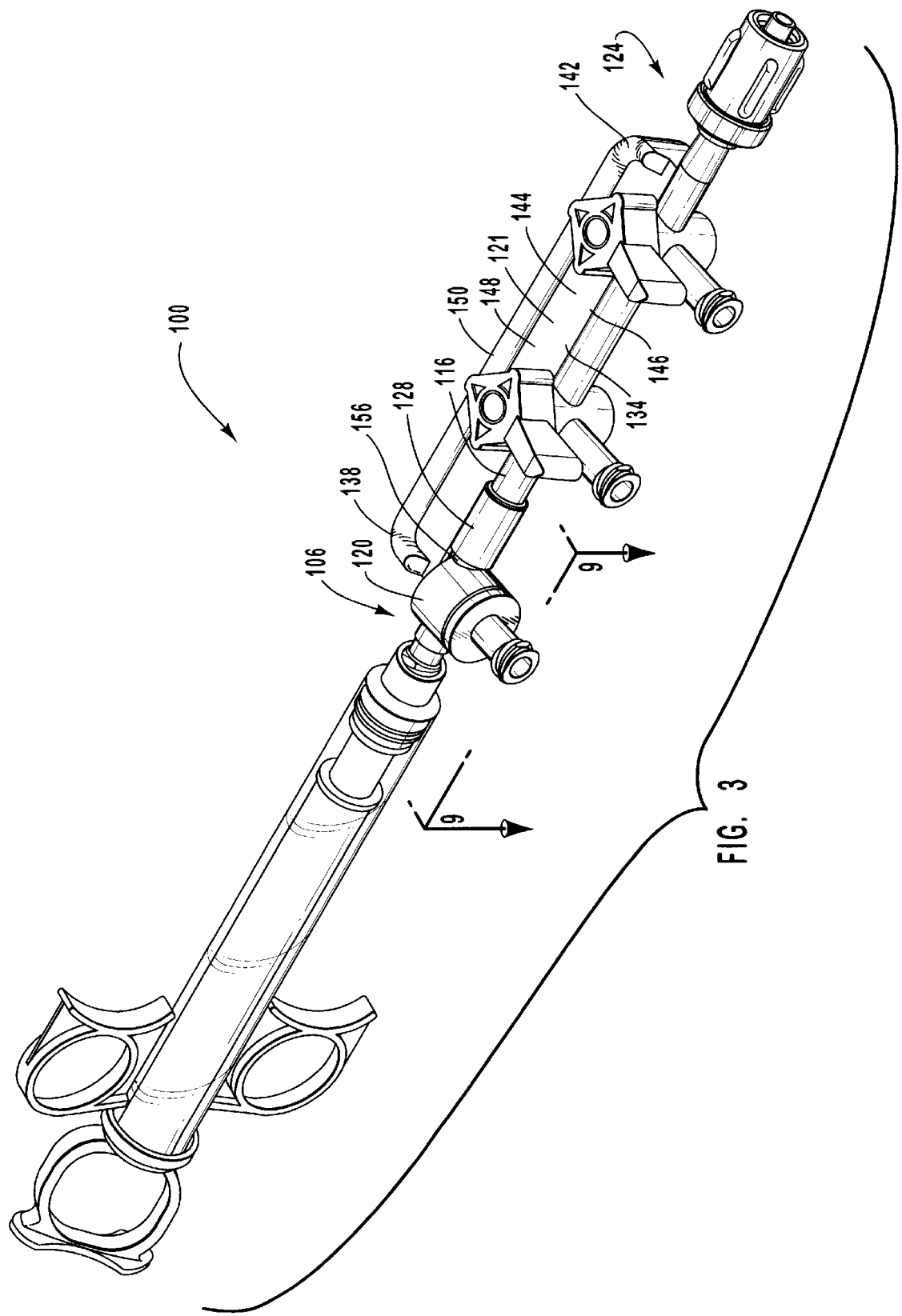
FIG. 3 is a perspective view of the fluid administration set shown in FIG. 2.

With reference now to FIGS. 2 and 3, a medical fluid administration set 100 of the present invention is shown. Medical fluid administration set 100 comprises (i) a syringe 102, and (ii) a manifold 104. Manifold 104 comprises (i) a manifold body 108 having a proximal end 122 and a distal end 124; (ii) means for coupling the proximal end 122 of manifold body 108 in fluid communication with fluid delivery means for delivering fluid to manifold body 108 (e.g., syringe 102); and (iii) means for coupling distal end 124 of manifold body 108 in fluid communication with means for receiving fluid from manifold body 108, such as a catheter (not shown) to be placed into the circulatory system of the patient.

Manifold body 108 defines a fluid flow pathway extending between proximal and distal ends 122, 124 of manifold body 108. Manifold body 108 also includes a check valve 106, and one or more valves 110, 112 coupled thereto. Manifold body 108 comprises means for coupling check valve 106 to second valve 110 such that check valve 106 is in fluid communication with second valve 110. Manifold body 108 further comprises means for coupling second valve 110 in fluid communication with third valve 112.

An example of such means for coupling check valve 106 to second valve 110 shown in FIGS. 2 and 3 includes a first tube 116 coupled between second valve 110 and check valve 106. As an example of means for coupling valves 110, 112, a second tube 114 is coupled between second valve 110 and third valve 112. In the embodiment of FIGS. 2 and 3, second and third valve 110, 112 comprise stopcock-actuated valves, although a variety of different valves are available within body 108. By selectively opening second valve 110, check valve 106 is in fluid communication with third valve 112.

In the embodiment of FIGS. 2 and 3, the fluid flow pathway of manifold body 108 is defined by (i) valves 106, 110, 112; (ii) tube 116; (ii) tube 114; and third tube 118 coupled to second valve 112 and a rotating adaptor 126, or other means for selectively coupling manifold 104 in fluid communication with a catheter. However, the fluid flow pathway can be defined by a variety of different members such as through the use of a check valve and another valve, or through the use of four or more valves.

Each of tubes 114, 116, 118 can have a variety of different cross sectional shapes, including circular, rectangular, square and a variety of other shapes. In one embodiment, check valve is selectively coupled to a fluid delivery means, e.g., syringe 102 and to a source of contrast fluid, while second valve 110 is selectively coupled to a source of saline solution, and third valve 112 is selectively coupled to a pressure monitor, for example. Upon orienting the handles of the stopcocks of valves 110, 112 upwardly as shown in FIGS. 2 and 3, fluid dispelled from syringe 102 flows through tubes 116, 114 and 118 and into a catheter coupled to distal end 124.

The orientation of check valve 106 within manifold body 108 fosters an improved, reinforced connection between check valve 106 and the remaining structures of manifold body 108. In light of the positioning of check valve 106 within body 108, check valve 106 is protected from damage during bending of syringe 102 and compression of the syringe plunger.

The connection between check valve 106 and such structures within body 108 is also reinforced by providing support means coupled to first tube 116 and check valve 106 for supporting check valve 106. Check valve 106 comprises a housing having a main valve chamber 120 and a plurality of ports coupled to main valve chamber 120. A variety of different examples of support means are available for supporting check valve 106, including for example, a seat 132 coupled to main chamber 120 and tube 116.

Seat 132 is configured to receive a portion of valve 106 in mating relationship. Tube 116 includes a collar 128 sized to receive an exit port 156 (FIG. 3) of valve 106. Seat 132 is coupled to collar 128 and is configured to receive a portion of main chamber 120 of valve 106 in mating relationship.

Another example of a support means includes a support member 121 coupled to check valve main chamber 120. In the embodiment of FIGS. 2 and 3, support member 121 is coupled to seat 132. Support member 121 of FIGS. 2 and 3 is also coupled to tubes 114, 116, 118 and to valves 106, 110, and 112 of manifold body 108. It will be appreciated, however, that support member 121 may be merely coupled to one or more tubes, and/or one or more valves, depending on the embodiment of the manifold desired.

A first end 134 of support member 121 is coupled along the longitudinal length of the manifold body 108 while a second end 136 thereof is free. Proximal terminus 138 of support member 121 is coupled to the lower surface 140 of seat 132 of manifold body 108, thereby providing support to seat 132 and main chamber 120 of valve 106. A distal terminus 142 of support member 121 is coupled to distal end 124 of manifold body 108.

Support member 121 comprises a rigid plate 144 having a first end 146 coupled along the longitudinal length of manifold body 108. A second end 148 of plate 144 has a beam 150 coupled along the longitudinal axis thereof. Beam 150 assists plate 144 in strengthening the connection between valve and manifold body.

With reference now to FIG. 4, an exploded view of manifold body 104 is shown. As mentioned, check valve 106 has a housing 151 comprising: (i) a main valve chamber 120, (ii) a first port 152 coupled to main valve chamber 120; (iii) a second port 154 coupled to main valve chamber 120, and (iv) a third port 156 coupled to main valve chamber 120. As will be discussed in additional detail below, housing 151 is an example of housing means for defining first, second and third fluid flow passageways.

Collar 128 of tube 116 receives and surrounds third port 156 of valve 106 while seat 132 coupled to collar 128 receives a lower portion of main valve chamber 120 in mating relationship. This aligns valve 106 such that port 152 is in alignment with ports 158, 160 of body 108.

Ports 152, 154 have male Luer lock components or female Luer lock components thereon or other means for selectively coupling ports 152, 154 to desired structures. Preferably port 154 is configured to be selectively coupled in fluid communication with a fluid delivery means, such as syringe 102, port 152 is configured to be selectively coupled in fluid communication with a contrast fluid source, and port 156 is configured to be coupled to seat 132 and collar 128 of manifold body 108. In one embodiment, port 156 and collar 128 are joined permanently through the use of an adhesive, such as chemical adhesives, or by friction welding, ultrasonic welding, or other means known in the art. Port 156 and collar 128 can also be integrally formed.

FIG. 4 also demonstrates the valve casings 162, 164 of manifold body 108 which receive respective stopcocks 166, 168 of valves 110, 112. Manifold 104 further comprises means on manifold body 108 for coupling a catheter in fluid communication with manifold body 108. Adaptor 126 having a male or female Luer lock component or other suitable connector may be employed as an example of means on the manifold body for selectively coupling a catheter to manifold body 108.

FIGS. 5 and 6 provide additional views of seat 132 and collar 128 of manifold body 108 and of the support member 121 coupled thereto. As shown in FIG. 5, in one embodiment, the support member 121 has a beam 150, the sides of which extend on opposing sides of free end 148 of support plate 144, thereby providing support and reinforcement to support plate 144.

FIG. 6 demonstrates support member 121 being disposed below receiving seat 132, thereby providing support and reinforcement to main valve chamber 120 of valve 106. Each of FIGS. 4, 5, and 6 demonstrate the support provided to main valve chamber 120 by support plate 144, seat 132, and collar 128. This support reinforces the connection between valve 106 and the remainder of manifold body 108.

While a variety of different check valves may be employed in the present invention, the check valves having a variety of different components and fluid flow paths, check valve 106 of FIGS. 2–10, will now be described in additional detail by way of example. With reference now to FIGS. 7 and 8, check valve 106 is shown in exploded and cross sectional views.

Main chamber 120 of valve 106 includes a body portion 170 and a cap 172. Cap 172 has first port 152 coupled thereto while body 170 has a second port 154 and a third port 156 coupled thereto. Second and third ports 154, 156 are each coupled on opposing sides of body 170 of valve 106. Each of said first, second, and third ports 152, 154, 156 define a fluid passageway therethrough. Thus, as mentioned, check valve housing 151 is an example of housing means for defining first, second and third fluid flow passageways.

Check valve 106 further comprises valving means for responding to a pressure laden fluid within one passageway to open another passageway and simultaneously close yet another passageway. As shown, the valving means of FIGS. 7 and 8 includes a valve head 174. Valve head 174 is preferably a flexible, elastomeric membrane, which responds to pressure laden fluid flowing through ports 152, 154, 156. Valve head 174 is preferably a hexagonal shaped member. This shape is preferred in order to allow valve head 174 to be properly oriented within main chamber 120 such that valve head 174 seals a desired fluid pathway, but also such that fluid flows past the sides of valve head 174 when desired.

Once valve head 174 is placed within body 170, body 170 and valve cap 172 are joined together by mutually accommodating ridges and grooves by application of an adhesive, such as chemical adhesives, or by friction welding, ultrasonic welding, or other means known in the art.

Figure 9:
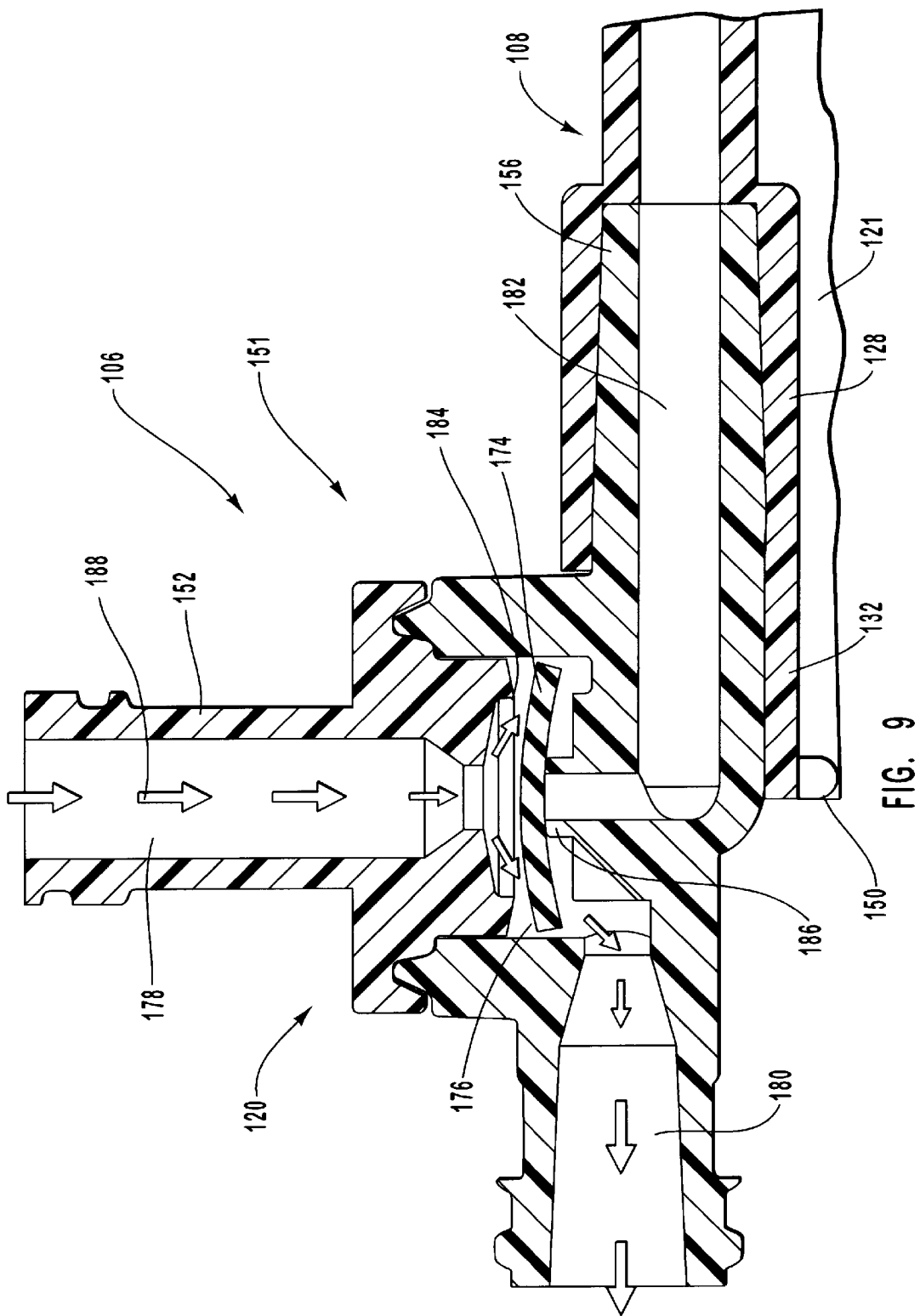
FIG. 9 is a cross-sectional view of the valve shown in FIG. 7 showing the fluid input path from a contrast fluid source to a syringe.
Figure 10:
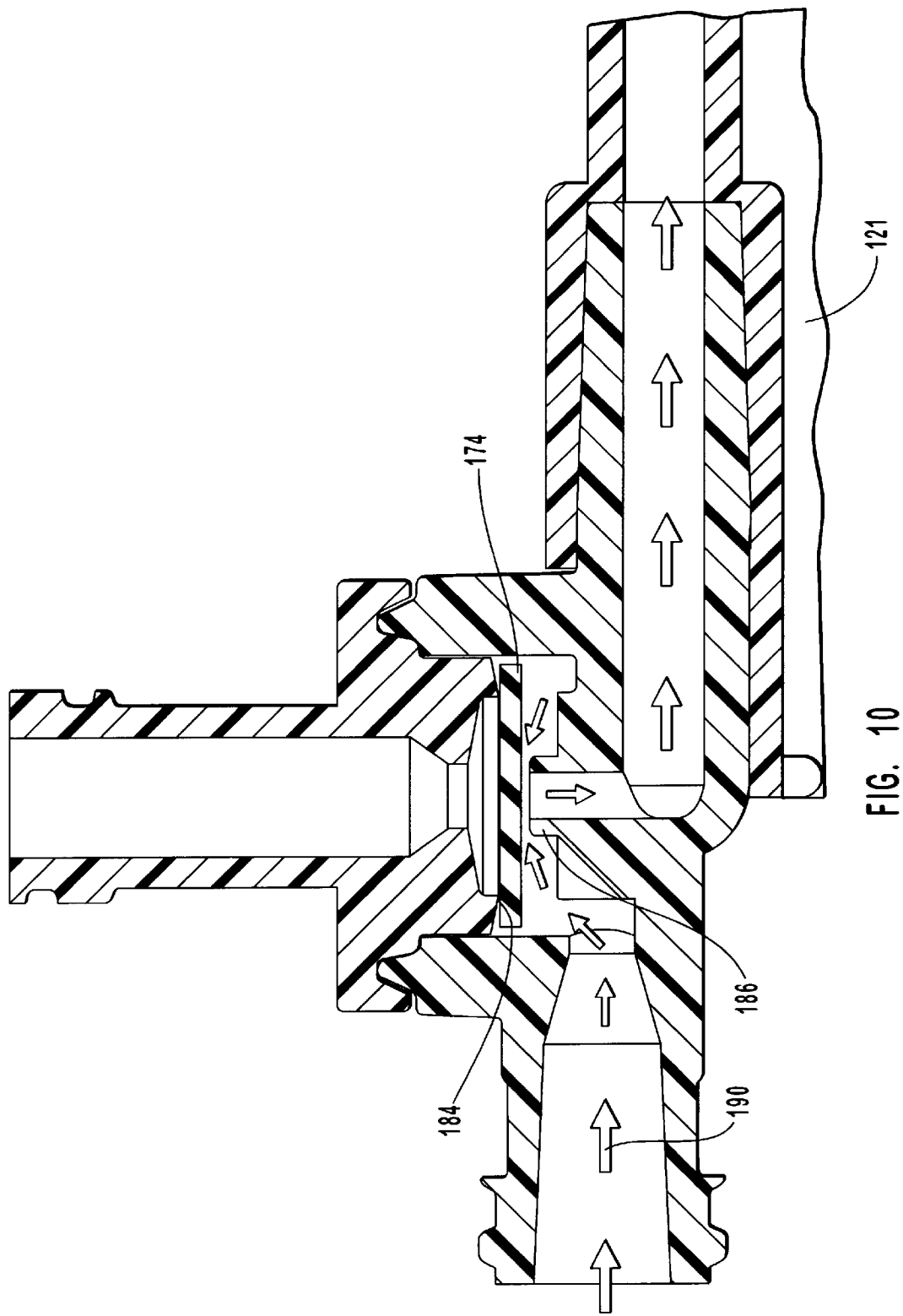
FIG. 10 is a cross-sectional view of the valve shown in FIG. 9 demonstrating the fluid output path from a syringe through the manifold.

With reference now to FIGS. 9 and 10, in the embodiment shown, check valve housing 151 further defines a common passageway intersection cavity 176 within main chamber 120 in which first, second, and third passageways 178, 180, 182 intersect. Valve head 174 responds to a pressure laden fluid within first passageway 178 to selectively open second passageway 180 and simultaneously close third passageway 182. Thus, fluid in the first passageway 178 flows from first passageway 178, through the intersection cavity 176, and into the second passageway 180 without entering third passageway 182. Valve head 174 also responds to a pressure laden fluid flowing into the intersection cavity 176 from second passageway 180 to seal first passageway 178 and to open third passageway 182.

In the embodiment of FIGS. 9 and 10, the valving means further comprises first and second valve seat means for providing first and second sealing surfaces. By way of example, the first and second valve seat means shown for providing first and second sealing surfaces are respectively depicted as circular first valve seat 184 and circular second valve seat 186. Upon flow of fluid through valve, valve head 174 contacts either the first or second sealing surface so as to seal or open a selected passageway.

The valving means is situated in intersection cavity 176. As shown, third port 156 of check valve 106 is coupled to collar 128 of tube 116 such that third passageway 182 is in fluid communication with second valve 110. Tube 116 is an example of means for coupling the check valve 106 to second valve 110 such that third passageway 182 of check valve 106 is in fluid communication with second valve 110.

In order for valve head 174 to be positioned so as to allow a pressure laden fluid to flow from one passageway through the common channel intersection cavity 176 and into another passageway, a predetermined crack pressure must be realized in the pressure laden fluid so as to break the seal between valve head 174 and the corresponding valve seat.

To better increase the crack pressure needed to deform valve head 174 in such a manner, in one embodiment, first valve seat 184 is beveled with respect to the longitudinal axis of valve 106, such as by being beveled 12° with respect to the longitudinal axis of valve 106. Similarly, in one embodiment, second valve seat 186 is beveled with respect to the longitudinal axis of valve 106, such as by being beveled 15° with respect to the longitudinal axis of valve 106. Thus, valve head 174 is contacted by the beveled part of the respective valve seat. These beveled surfaces serve to better seal the channels and to increase the resultant crack pressure of valve head 174.

The pressure required to deform valve head 174 so as to allow fluid to flow past valve head 174 must be both a pressure to overcome opposing fluid pressures in other channels plus the predetermined crack pressure applicable thereto. For example, valve head 174 seals third passageway 182 when the pressure in first passageway 178 is greater than the pressure in second passageway 180 or third passageway 182 (or is greater than the pressure in second passageway 180 and the pressure in third passageway 182 is not greater than ambient), whereby the fluid flows from first passageway 178 through the intersection cavity 176 of the three passageways and into second passageway 180 without entering third passageway 182. Also, valve head 174 seals first passageway 178 when the pressure in second passageway 180 is greater than the pressure in either first passageway 178 or third passageway 182 (or is greater than the pressure in first passageway 178 and the pressure in third passageway 182 is not greater than ambient). Then, the fluid in second passageway 180 flows therefrom through the intersection cavity 176 of the three passageways and into third passageway 182 without entering first passageway 178, which has been sealed off by valve head 174.

Referring to FIG. 9, as the practitioner retracts the plunger of syringe 102, fluid from the contrast fluid source or other fluid source flows through first port 152 into syringe 102 along ingress path 188. With reference now to FIG. 10, upon then desiring to insert contrast dye fluid into the circulatory system of the patient, the practitioner inserts the plunger into the syringe barrel, thereby forcing fluid from syringe 102 into manifold along egress path 190.

Although these fluid paths have been shown by way of example in FIGS. 9 and 10, it will be appreciated that a variety of different fluid paths may be employed and a variety of different configurations of a check valve and valving means (including more than one valve head for example) may be employed in the present invention.

Referring now to FIGS. 11 and 12, in another embodiment of a manifold 200, manifold body 202 features a check valve 204 integrally coupled to a first tube 210. Tube 210 is integrally coupled between check valve 202 and second valve 206, while a second tube 212 is integrally coupled between second valve 206 and third valve 208. A support plate 218 is coupled integrally to the main valve chamber 219 of check valve 204, and to second valve 206, third valve 208, first tube 210, second tube 212 and third tube 216. A cross sectional view of the integrally coupled check valve 204 is featured within FIG. 13.

Fluid flows through manifold 200 in the same or similar manner as discussed above with respect to manifold 104. This embodiment is advantageous because the connection between check valve 204 and the remainder of manifold body 202 and support plate 218 is an integral connection, further preventing damage through breaking or cracking of the connection between valve 204 and the remainder of manifold body 202 during use.

Valve head 174 should be comprised of materials which function equally well with saline, contrast media, heparinized saline, or with whole blood. Valve head 174 preferably has low or no lipid interaction and is transparent and either light or clear in color. The materials from which manifold 104 and manifold 200 are constructed are preferably polyvinylchloride, polycarbonate, or other suitable medical grade plastic.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A manifold, comprising:

a manifold body having a proximal end and a distal end, the manifold body defining a fluid flow pathway extending between the proximal and distal ends of the manifold body, the manifold body including a plurality of valves, at least one valve having (i) housing means for defining first, second and third fluid flow passageways, each of said passageways intersecting in a common passageway intersection cavity; and (ii) valving means situated within the intersection cavity for responding to a pressure laden fluid within one passageway to open another passageway and simultaneously close yet another passageway;

means for coupling the proximal end of the manifold body in fluid communication with fluid delivery means for delivering fluid to the manifold body; and means for coupling the distal end of the manifold body in fluid communication with means for receiving fluid flowing from the fluid flow pathway of the manifold body.

2. A manifold as recited in claim 1, wherein the valving means comprises means for responding to a pressure laden fluid within the first passageway to selectively open the second passageway and simultaneously close the third passageway, such that fluid in the first passageway flows from the first passageway, through the intersection cavity, and into the second passageway without entering the third passageway, wherein the valving means also responds to a pressure laden fluid flowing into the intersection cavity from the second passageway to seal the first passageway and to open the third passageway.

3. A manifold as recited in claim 1, wherein one of the valves of the manifold body comprises a stopcock-actuated valve.

4. A manifold as recited in claim 3, wherein the manifold body further comprises means for coupling the housing means of the at least one valve to the stopcock-actuated valve such that the stopcock-actuated valve is in fluid communication with the third passageway of the housing means.

5. A manifold as recited in claim 1, further comprising support means coupled to the housing means of the at least one valve for supporting the housing means.

6. A manifold as recited in claim 5, wherein the support means comprises the manifold body including a seat coupled to housing means.

7. A manifold as recited in claim 5, wherein the support means comprises a support member coupled to the housing means.

8. A manifold as recited in claim 7, wherein the support member comprises a rigid support plate.

9. A manifold, comprising:

a manifold body having a proximal end and a distal end, the manifold body defining a fluid flow pathway extending between the proximal and distal ends of the manifold body, the manifold body including a check valve, a second valve, and means for coupling the check valve to the second valve such that the check valve is in fluid communication with the second valve;

means for coupling the proximal end of the manifold body in fluid communication with fluid delivery means for delivering fluid to the manifold body; and means for coupling the distal end of the manifold body in fluid communication with means for receiving fluid flowing from the fluid flow pathway of the manifold body.

10. A manifold as recited in claim 9, wherein the means for coupling the check valve to the second valve comprises a tube coupled between the second valve and the check valve.

11. A manifold as recited in claim 10, wherein the tube is integrally coupled between the second valve and the check valve.

12. A manifold as recited in claim 9, wherein the second valve comprises a stopcock-actuated valve.

13. A manifold as recited in claim 9, wherein the check valve is coupled to the fluid delivery means.

14. A manifold as recited in claim 9, wherein the manifold body further comprises a third valve; and (ii) means for coupling the second and third valves such that the second and third valves are in fluid communication.

15. A manifold as recited in claim 9, wherein the check valve comprises a main valve chamber and a plurality of ports coupled to the main valve chamber.

16. A manifold as recited in claim 15, further comprising support means coupled to the main valve chamber of the check valve for supporting the main valve chamber of the check valve.

17. A manifold as recited in claim 16, wherein the support means comprises the manifold body including a seat coupled to the main valve chamber of the check valve.

18. A manifold as recited in claim 16, wherein the support means comprises a support member coupled to (i) the means for coupling the check valve to the second valve and (ii) the main valve chamber of the check valve.

19. A manifold as recited in claim 16, wherein the support means comprises a rigid support plate coupled to the second valve and the main chamber of the check valve.

20. A manifold as recited in claim 9, wherein the check valve has (i) a housing defining a first fluid flow passageway, a second fluid flow passageway, and a third fluid flow passageway, each of said passageways intersecting in a common passageway intersection cavity; and (ii) valving means situated within the intersection cavity for responding to a pressure laden fluid within the first passageway to selectively open the second passageway and simultaneously close the third passageway, such that fluid in the first passageway flows from the first passageway, through the intersection cavity, and into the second passageway without entering the third passageway, wherein the valving means also responds to a pressure laden fluid flowing into the intersection cavity from the second passageway to seal the first passageway and to open the third passageway.

21. A catheter manifold, comprising:

(i) a manifold body having a proximal end and a distal end, the manifold body defining a fluid flow pathway extending between the proximal and distal ends of the manifold body, the manifold body including:

(A) a first valve having
  (1) a housing defining a first fluid flow passageway, a second fluid flow passageway, and a third fluid flow passageway, each of said fluid flow passageways intersecting in a common passageway intersection cavity; and
  (2) valving means situated in the intersection cavity for responding to a pressure laden fluid within the first passageway to selectively open the second passageway and simultaneously close the third passageway, such that fluid in the first passageway flows from the first passageway, through the intersection cavity, and into the second passageway without entering the third passageway, wherein the valving means also responds to a pressure laden fluid flowing into the intersection cavity from the second passageway to seal the first passageway and to open the third passageway; and
(B) a second valve coupled to the first valve such that the third passageway of the first valve is in fluid communication with the second valve;
(ii) means for coupling the proximal end of the manifold body in fluid communication with fluid delivery means for delivering fluid to the manifold body; and
(iii) means for coupling the distal end of the manifold body in fluid communication with a catheter.

22. A manifold as recited in claim 21, wherein the first valve comprises a check valve.

23. A manifold as recited in claim 21, wherein the second valve comprises a stopcock-actuated valve.

24. A catheter manifold, comprising:
(i) a manifold body having a proximal end and a distal end, the manifold body defining a fluid flow pathway extending between the proximal and distal ends of the manifold body, the manifold body including:
  (A) a check valve having a main valve chamber; and
  (B) a second valve coupled to the check valve such that the check valve is in fluid communication with the second valve; and
(ii) means for coupling the proximal end of the manifold body in fluid communication with fluid delivery means for delivering fluid to the manifold body; and
(iii) means for coupling the distal end of the manifold body in fluid communication with a catheter.

25. A manifold as recited in claim 24, further comprising support means coupled to the main valve chamber of the check valve for supporting the main valve chamber of the check valve.

26. A manifold as recited in claim 25, wherein the support means for supporting the main valve chamber of the check valve comprises a support member coupled to the second valve and the main valve chamber of the check valve.

27. A manifold as recited in claim 26, wherein the support means for supporting the main valve chamber of the check valve comprises a rigid support plate.

28. A manifold as recited in claim 25, wherein a tube is coupled to the check valve and the second valve such that the second valve is in fluid communication with the check valve.

29. A manifold as recited in claim 28, wherein the support means for supporting the main valve chamber of the check valve comprises the manifold body including a seat coupled to the main valve chamber of the check valve and to the tube.

30. A manifold as recited in claim 28, wherein the support means for supporting the main valve chamber of the check valve comprises a support member coupled to the tube and the main valve chamber of the check valve.

31. A manifold as recited in claim 28, wherein the support means for supporting the main valve chamber of the check valve comprises a rigid support plate coupled to the tube and the main valve chamber of the check valve.

32. A manifold as recited in claim 31, wherein the rigid support plate is coupled at one end thereof to the manifold body, and wherein the support means further comprises a beam coupled to an opposing end of the rigid support plate along the longitudinal axis thereof.

33. A manifold as recited in claim 28, wherein the support means for supporting the main valve chamber of the check valve comprises
  a seat configured to receive a portion of the main valve chamber of the check valve, the seat being coupled to the tube; and
  a rigid support plate coupled to the tube and the seat.

34. A catheter manifold, comprising:
(i) a manifold body having a proximal end and a distal end, the manifold body defining a fluid flow pathway extending between the proximal and distal ends of the manifold body, the manifold body including:
  (A) a check valve having a main valve chamber;
  (B) a stopcock-actuated valve; and
  (C) a tube coupling the check valve to the stopcock-actuated valve such that the check valve in fluid communication with the stopcock-actuated valve; and
(ii) means for coupling the proximal end of the manifold body in fluid communication with fluid delivery means for delivering fluid to the manifold body; and
(iii) means for coupling the distal end of the manifold body in fluid communication with a catheter.

35. A catheter manifold as recited in claim 34, wherein the tube is integrally coupled between the check valve and the stopcock-actuated valve.

* * * * *